(12) United States Patent
Drammeh

(10) Patent No.: US 9,558,647 B1
(45) Date of Patent: Jan. 31, 2017

(54) EMPLOYEE HYGIENE ASSURANCE SYSTEM

(71) Applicant: Sheikh Moussa Drammeh, Bronx, NY (US)

(72) Inventor: Sheikh Moussa Drammeh, Bronx, NY (US)

( * ) Notice: Subject to any disclaimer, the term of this patent is extended or adjusted under 35 U.S.C. 154(b) by 0 days.

(21) Appl. No.: 14/316,077

(22) Filed: Jun. 26, 2014

(51) Int. Cl.
*G08B 21/24* (2006.01)

(52) U.S. Cl.
CPC .................................. *G08B 21/245* (2013.01)

(58) Field of Classification Search
CPC ....................................................... G08B 21/245
See application file for complete search history.

(56) References Cited

U.S. PATENT DOCUMENTS

| 3,938,120 | A | | 2/1976 | O'Connell |
| 4,606,085 | A | | 8/1986 | Davies |
| 5,610,589 | A | | 3/1997 | Evans et al. |
| 5,808,553 | A | * | 9/1998 | Cunningham ....... G08B 21/245 340/528 |
| 5,952,924 | A | | 9/1999 | Evans et al. |
| 6,236,317 | B1 | | 5/2001 | Cohen et al. |
| 6,523,193 | B2 | | 2/2003 | Saraya |
| 6,727,818 | B1 | | 4/2004 | Wildman et al. |
| 6,975,231 | B2 | | 12/2005 | Lane et al. |
| 2009/0195385 | A1 | * | 8/2009 | Huang ................. G08B 21/245 340/572.1 |
| 2011/0057799 | A1 | * | 3/2011 | Taneff .................. G06F 19/327 340/573.1 |

FOREIGN PATENT DOCUMENTS

| EP | 0921506 | 6/1999 |
| GB | 2.425.388 | 10/2006 |
| WO | WO01/33529 | 5/2001 |
| WO | WO03/082351 | 10/2003 |

* cited by examiner

*Primary Examiner* — Leon Flores
(74) *Attorney, Agent, or Firm* — Michael I. Kroll; Edwin D. Schindler

(57) ABSTRACT

A hygiene assurance system utilizing a plurality of individual sensors having a correlating fixture or entrance, a keypad for identifying the user and a plurality of audible signals to ensure a user of a bathroom facility washes ones hands before leaving the area. Additionally the present invention provides sensors having individual controls for what predetermined parameters must be met to activate said sensor.

4 Claims, 15 Drawing Sheets

EMPLOYEE HYGIENE ASSURANCE SYSTEM

BACKGROUND OF THE INVENTION

Field of the Invention

The present invention relates generally to an employee hygienic assurance system and, more specifically, to a restroom facility incorporating ticket means that records and prints employee, date, time and whether sink water and soap where used during the bathroom session. The ticket is deposited in a ticket collection box for review by management.

The restroom facility incorporates a locked entry that requires an employee to key in their assigned key code to gain entrance into the restroom facility. A ticket dispenser within the facility is in communication with a door sensor so that when the door is unlatched a bathroom session ticket is initiated. Other facility sensors attached to the sink and soap dispenser denote on the bathroom session ticket whether sink water was used and whether soap was used.

Both sink sensor and soap sensor serving as indicators that the employee washed their hands during the bathroom session. When the door is again unlatched the ticket dispenser will produce a bathroom session ticket for the employee that will be deposited in a collection box upon leaving the restroom.

The bathroom facility further provides an exterior facility visual occupancy indicator and an interior message board that may display messages encouraging users to wash their hands or other reinforcing messages related to the need for personal hygiene.

Description of the Prior Art

There are other systems which provide for encouraging hygiene. While these systems may be suitable for the purposes for which they where designed, they would not be as suitable for the purposes of the present invention as heretofore described.

It is thus desirable to provide a bathroom facility with means for dispensing a bathroom session ticket to an employee denoting whether soap and water where used during their bathroom session, with the ticket then deposited into a collection box for review by management.

It is further desirable to provide the bathroom facility with a key pad lock and each employee with a unique ID that will be keyed into the key pad to gain entrance to the bathroom facility. Also provided is a ticket dispenser in communication with the door lock that initiates a bathroom session when the door is unlocked. Further provided are sensors in communication with the ticket dispenser that are attached to the sink supply line or drain indicating and denoting on the ticket water use and soap dispenser indicating the use of soap.

SUMMARY OF THE PRESENT INVENTION

A primary object of the present invention is to provide an employee hygiene assurance system to encourage employees to wash their hands after using the bathroom facility through a restroom session ticketing system that can be reviewed by management, which denotes whether soap and water were used during their bathroom session.

Another object of the present invention is to provide a hygiene assurance system having a bathroom facility with an entry door incorporating means of identifying the employee using the bathroom facility.

Yet another object of the present invention is to provide a hygiene assurance system wherein said employee identifying means is a unique key code assigned to each employee.

Still yet another object of the present invention is to provide a hygiene assurance system wherein said entry door has a key pad type lock, where the user will key in their unique key code to enter the bathroom facility.

An additional object of the present invention is to provide a hygiene assurance system further providing a ticket dispenser generating an employee bathroom session ticket when the employee uses the bathroom facility regardless of whether they use the toilet or not.

A further object of the present invention is to provide a hygiene assurance system that initiates a bathroom session ticket once an employee has keyed in their unique key code.

A yet further object of the present invention is to provide a hygiene assurance system having a plurality of sensors within the bathroom facility to detect the usage of hygiene services.

A still yet further object of the present invention is to provide a hygiene assurance system wherein said bathroom facility provides a sensor attached to the sink water ingress or egress line, which indicates that sink water was used during the employee bathroom session.

Another object of the present invention is to provide a hygiene assurance system where the sink water sensor is in electrical communication with the ticket dispenser.

Yet another object of the present invention is to provide a hygiene assurance system wherein said bathroom facility provides a sensor attached to the soap dispenser which indicates that soap was used during the employee bathroom session.

Still yet another object of the present invention is to provide a hygiene assurance system where the soap dispenser sensor is in electrical communication with the ticket dispenser.

An additional object of the present invention is to provide a hygiene assurance system having a ticket dispenser incorporating an electrical circuit having a power source, sensor signal receiver, microprocessor, memory storage, software/firmware and printer for generating a user bathroom session ticket.

A further object of the present invention is to provide a hygiene assurance system with an exterior facility visual occupancy indicator, preferably a lamp that is illuminated when the door is opened and turned off after the ticket is printed and the door closes.

A yet further object of the present invention is to provide a hygiene assurance system optionally providing a facility message board in electrical communication with said processor to encourage employees to wash their hands after using the bathroom facility.

Additional objects of the present invention will appear as the description proceeds.

The present invention overcomes the shortcomings of the prior art by providing a restroom facility incorporating ticket means that records and prints employee, date, time and whether sink water and soap where used during the bathroom session, where then the ticket is deposited in a ticket collection box for review by management.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
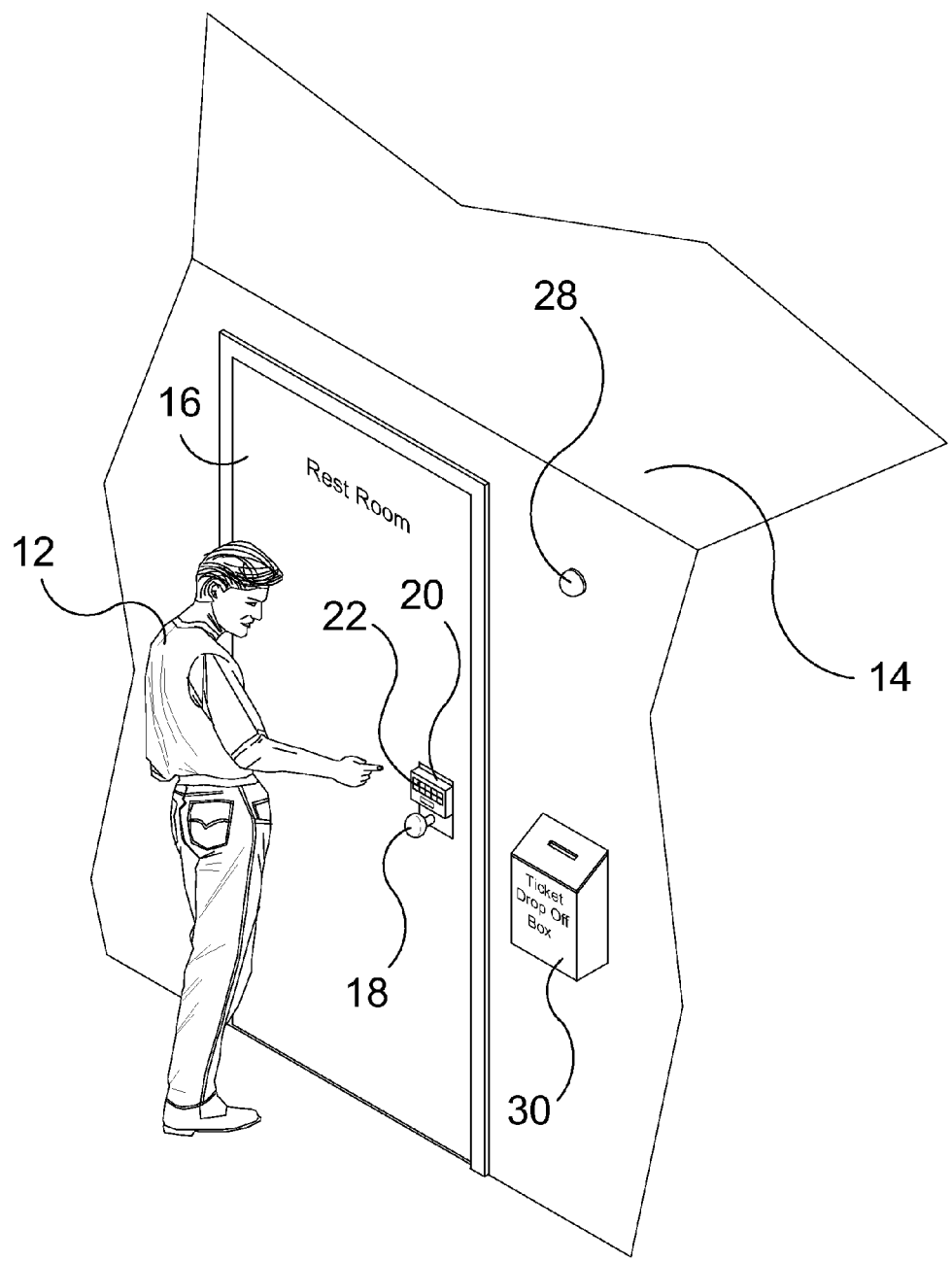
FIG. 1 is an illustrative view of a user entering their key code to enter the bathroom facility.

Turning now descriptively to the drawings, in which similar reference characters denote similar elements throughout the several views, the figures illustrate the Hygiene Assurance System of the present invention. With regard to the reference numerals used, the following numbering is used throughout the various drawing figures.

10 Hygiene Assurance System of the present invention
12 user
14 restroom facility
16 door
18 handle
20 lock
22 key pad of 20
24 transmitter of 20
26 signal of 20
28 occupancy indicator
30 ticket collection box
32 alarm/message display board
34 sink
36 water sensor
38 transmitter
40 signal of 36
42 soap dispenser
44 soap sensor
46 transmitter
48 signal of 44
50 ticket dispenser
52 power source
54 receiver
56 microprocessor
58 memory
60 software
62 printer
64 ticket

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Referring to FIG. 1, shown is an illustrative view of a user entering their key code to enter the bathroom facility. The restroom facility 14 incorporates a locked entry 16 that requires an employee 12 to key in their assigned key code into key pad 22 of lock 20 to gain entrance via handle 18. Also shown is a visual occupancy indicator 28.

Figure 2:
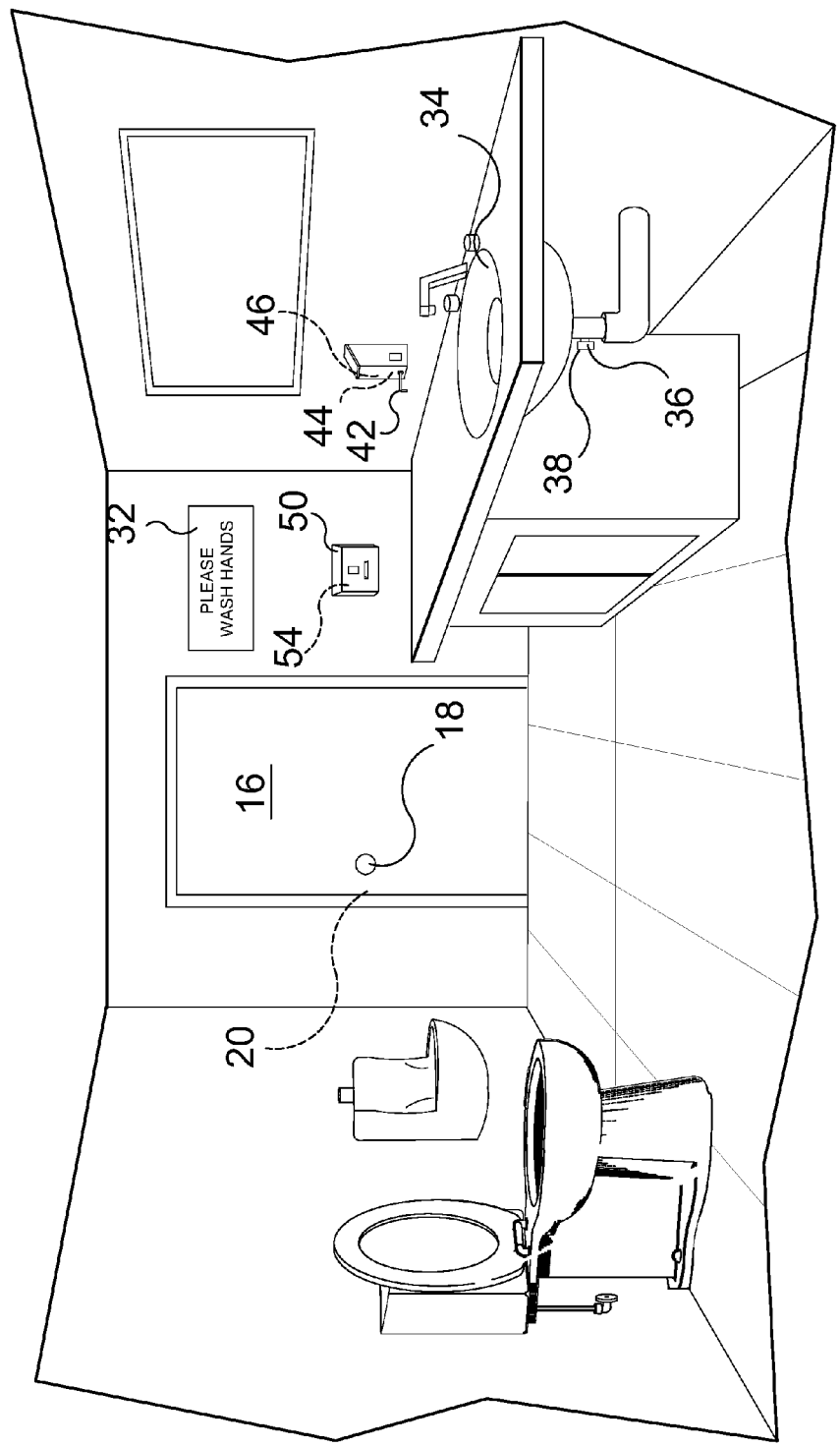
FIG. 2 is an illustrative view of a bathroom facility having hygiene services.

Referring to FIG. 2, shown is an illustrative view of a bathroom facility having hygiene services. Interiorly, the restroom facility provides a ticket dispenser 50 in communication with a door sensor so that when the door is unlatched a bathroom session ticket is initiated. Other facility sensors attached to the sink 34 and soap dispenser 42 when actuated serve as indicators that the employee washed their hands during the bathroom session. When the door is again unlatched the ticket dispenser 50 will produce a bathroom session ticket for the employee that will be deposited in a collection box 30, upon leaving the restroom.

Figure 3:
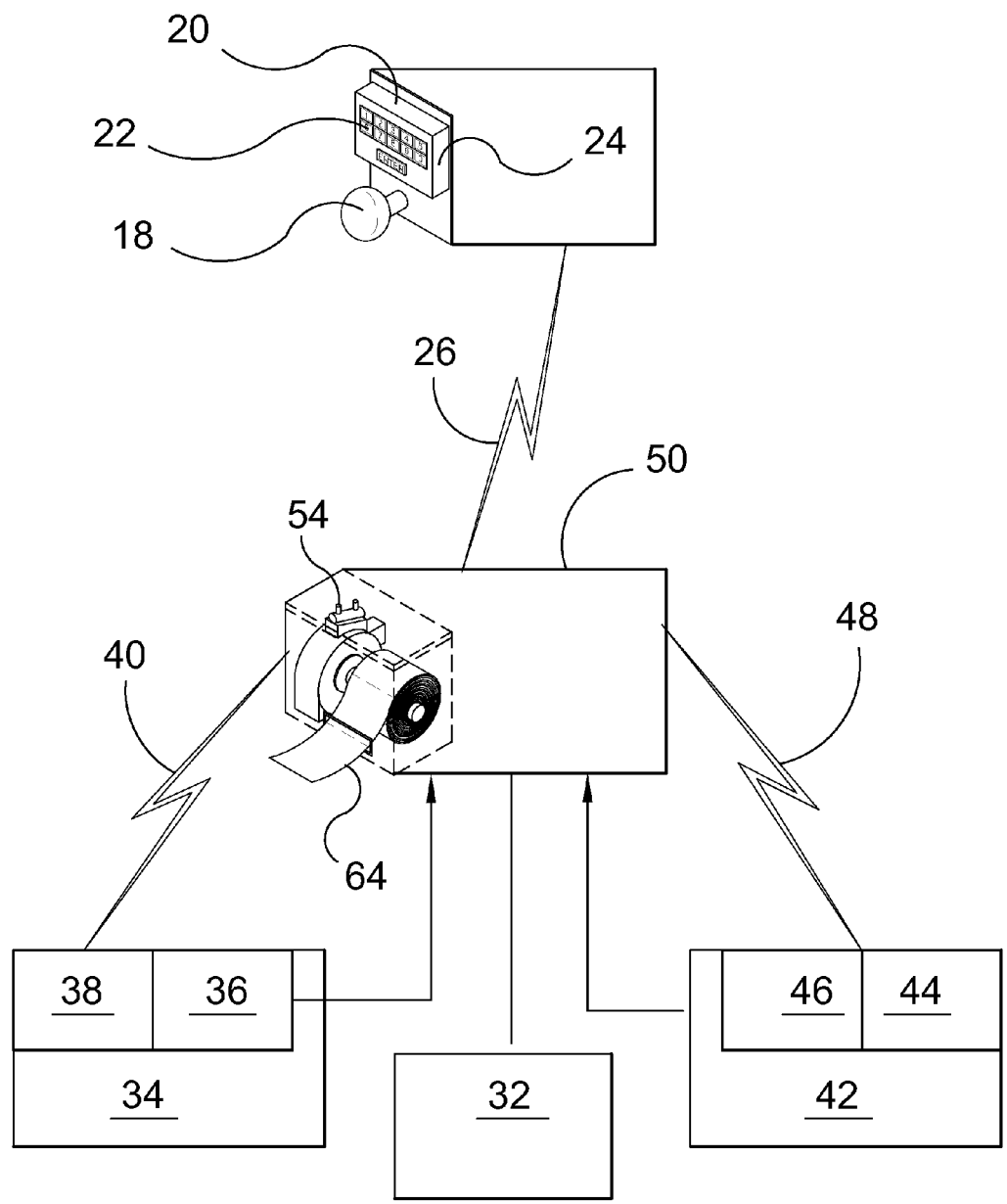
FIG. 3 is a chart depicting the bathroom facility services in communication with a bathroom session ticket dispenser.

Referring to FIG. 3, shown is a chart depicting the bathroom facility services in communication with a bathroom session ticket dispenser. The restroom facility incorporates an entry having knob 18 with lock 20 that requires an employee to key in their unique assigned key code onto key pad 22, which then generates signal 26 received by ticket dispenser 50 receiver 54 initiating an employee bathroom session ticket. To insure employee hygiene, a sensor 36 and transmitter 24 are attached to sink 34 so that when water is used signal 40 is generated and received by the ticket dispenser 50. Further provided is sensor 44 and transmitter 46 attached to soap dispenser 42 so that when soap is used signal 48 is generated and received by the ticket dispenser 50. It is undesirable to require an employee to enter key codes when exiting the bathroom facility, therefore, the lock is substantially an entry lock that records the ID of who is in the bathroom. Turning handle 18 to exit simply generates a signal that can be considered an end of session marker wherethen ticket dispenser 50 generates ticket 64. Optionally provided is message board 32 in electrical communication with said processor to encourage employees to wash their hands after using the bathroom facility.

Figure 4:
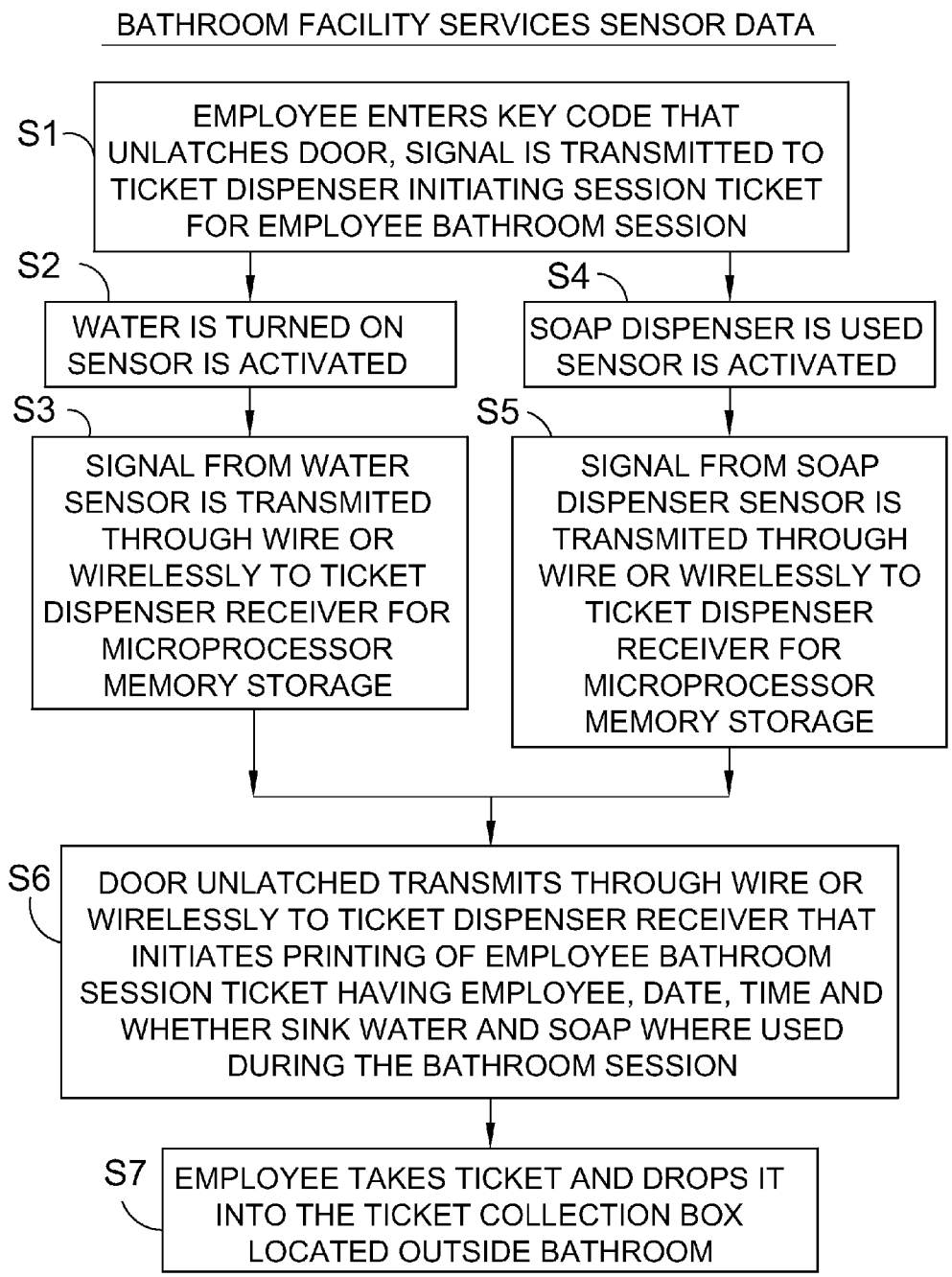
FIG. 4 is a block diagram illustrating steps for initiating a user bathroom session, recording services used, denoting services used when ticket generated, and disposition of ticket after generation.

Referring to FIG. 4, shown is a block diagram illustrating steps for initiating a user bathroom session, recording services used, denoting services used when ticket generated, and disposition of ticket after generation. The present invention uses sensors within a bathroom facility to generate bathroom session tickets that indicate whether sink water and soap where used during the bathroom session. The user is provided with a unique ID number so that in step S1, the employee enters their key code, which unlatches the door and transmits the key code to the ticket dispenser thereby uniquely identify the user. When the sink water is turned on, in step S2, the sink water sensor transmits a signal that is received by the ticket dispenser either through wire or wirelessly, as shown in step S3, which is then stored in the microprocessor memory until the ticket is printed. In step S4 when the soap dispenser is used, the soap sensor generates a signal that is sent either by wire or wirelessly, to the ticket dispenser that is then stored by the microprocessor in memory, as shown in step S5. In step S6, opening the door from the interior generates a signal received by the ticket dispenser that initiates printing of the employee's bathroom session ticket having employee, date, time, and whether water and soap where used during the bathroom session. When leaving the bathroom facility in step S7, the employee takes the ticket and drops it into a ticket collection box located outside the bathroom facility for management review.

Figure 5:
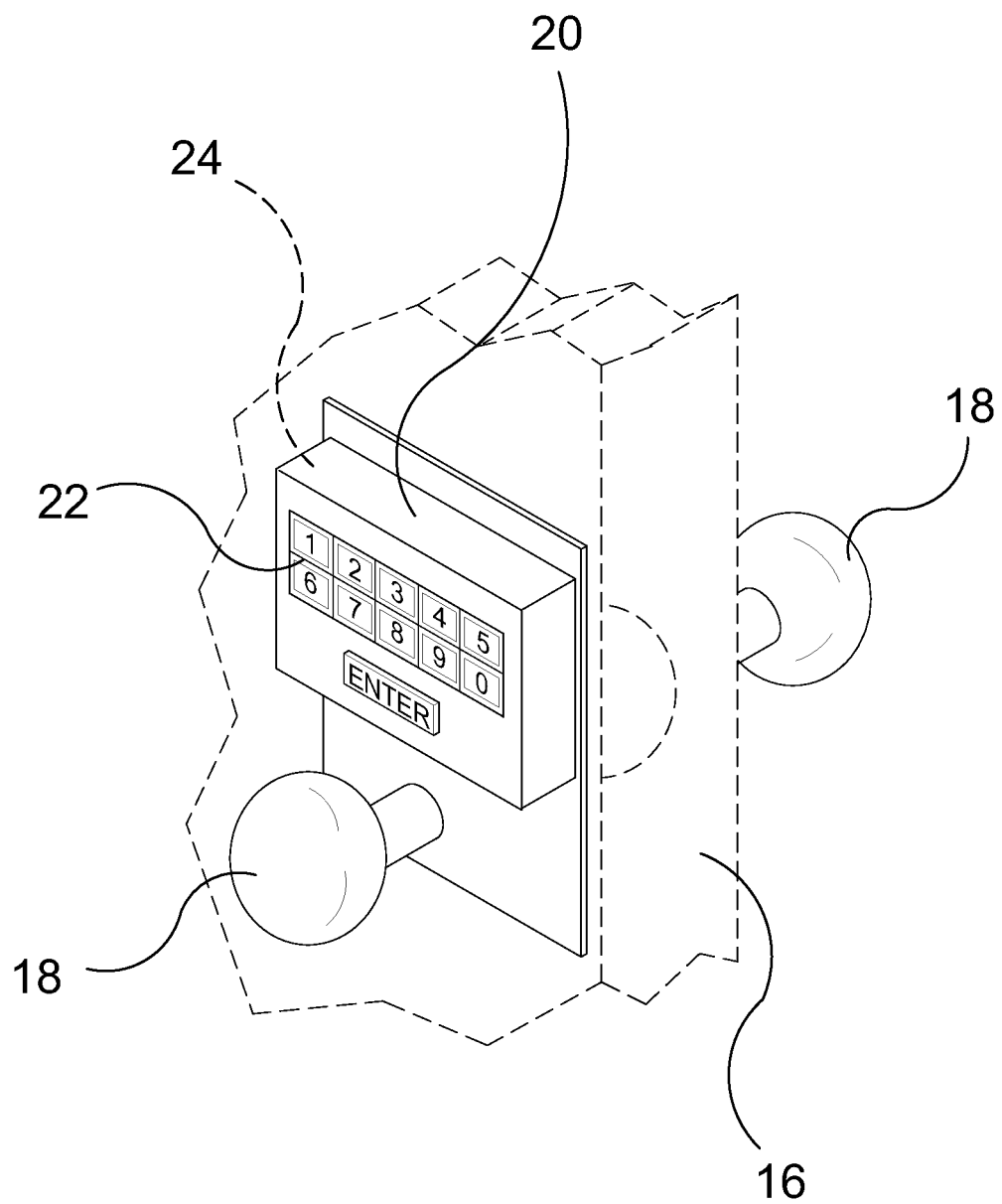
FIG. 5 is a perspective view of a lock having a key pad that may be used to identity the facilities user and initiate the generation of a bathroom session ticket.

Referring to FIG. 5, shown is a perspective view of a lock having a key pad that may be used to identity the facility's user and initiate the generation of a bathroom session ticket. The hygiene assurance system 10 of the present invention insures identity of each user by issuing unique ID numbers for each user so that when a user enters their unique ID on key pad 22 of lock 20, the door 16 unlocks and transmitter 24 generates a signal received by the ticket dispenser that initiates a bathroom session ticket for the user.

Figure 6:
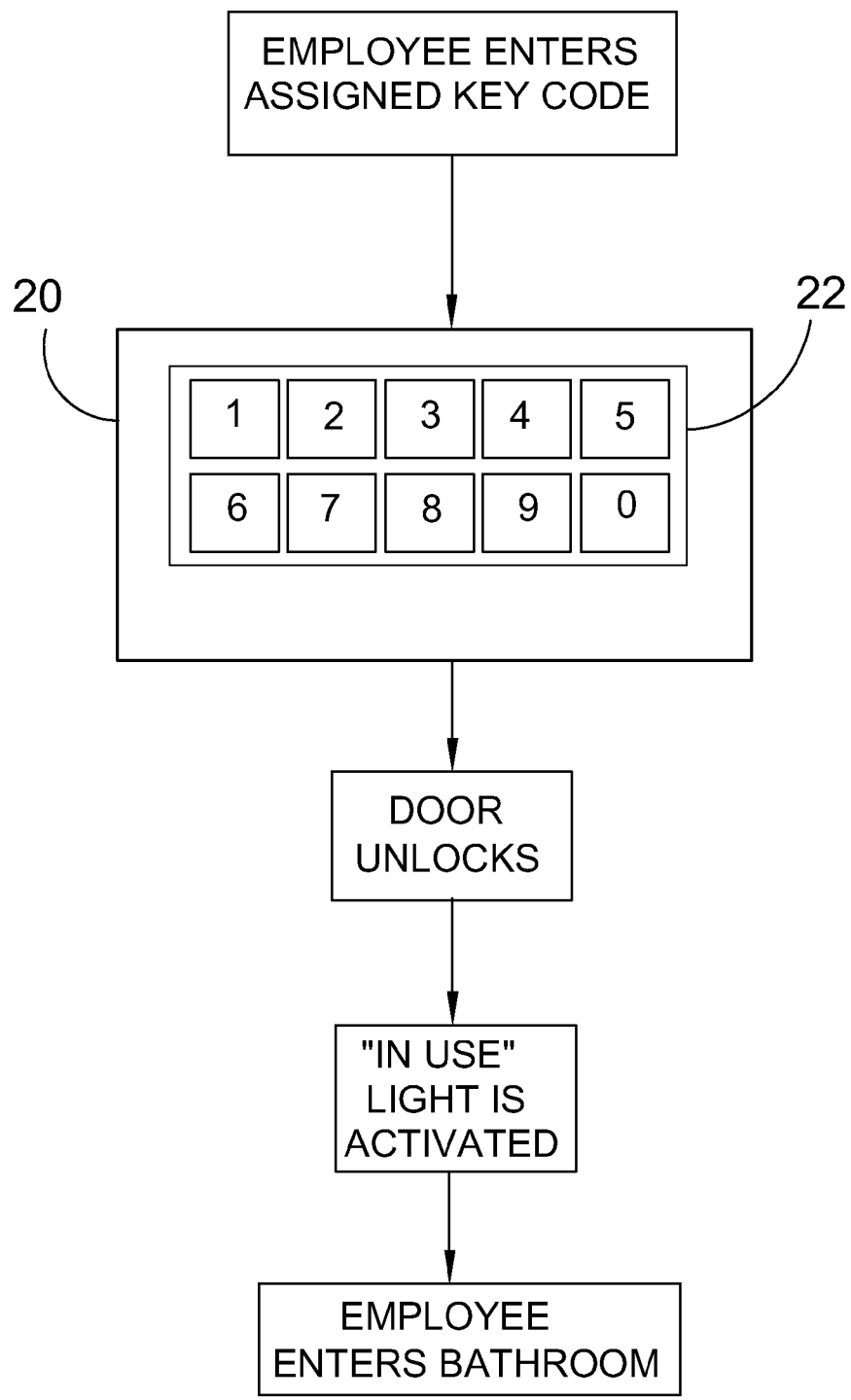
FIG. 6 is a block diagram of steps used to identify the bathroom facilities user.

Referring to FIG. 6, shown is a block diagram of steps used to identify the bathroom facilities user. The hygiene assurance system 10 of the present invention insures identity of each user by issuing unique ID numbers for each user so that when a user enters their unique ID on key pad 22 of lock 20, the door unlocks, the occupancy indicator is illuminated, the user enters the bathroom.

Figure 7:
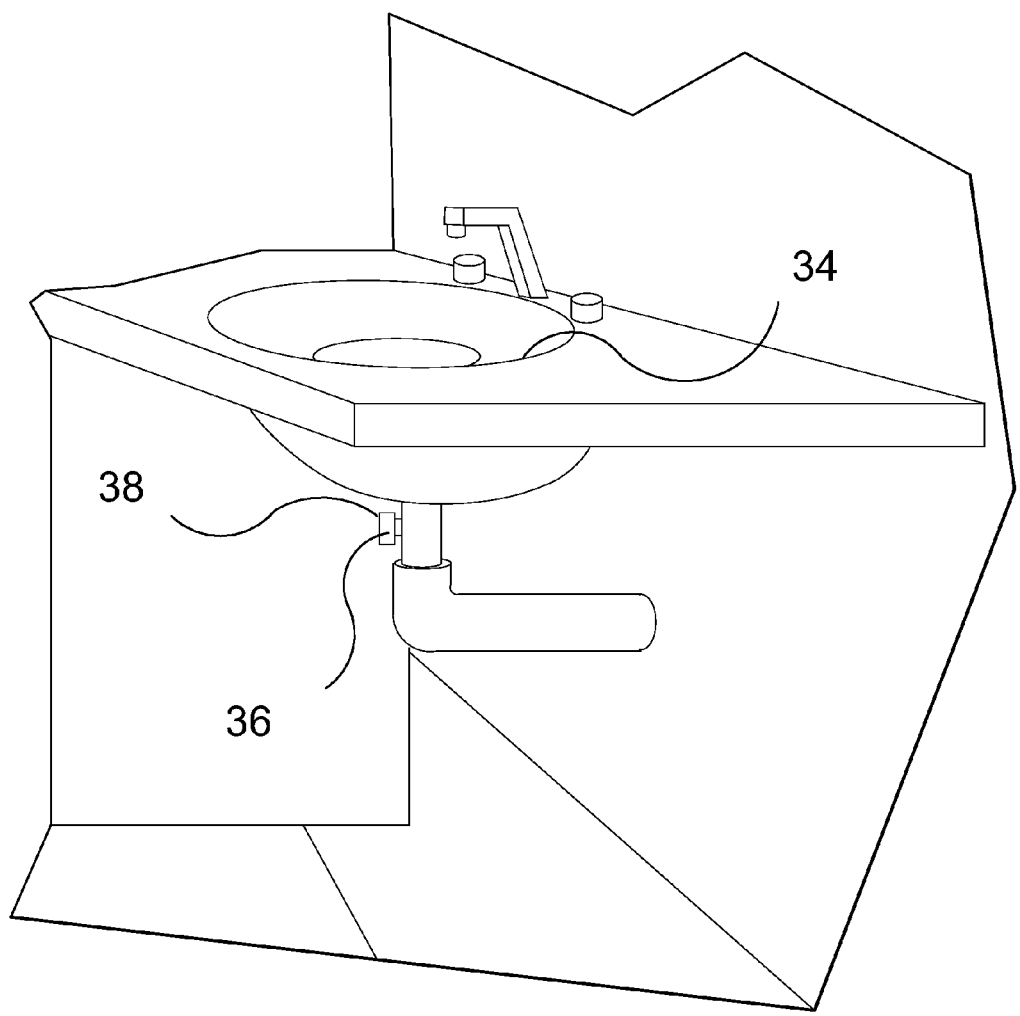
FIG. 7 is a perspective view of a sink having a sensor to detect and denote the use of water on a bathroom session ticket.

Referring to FIG. 7, shown is a perspective view of a sink having a sensor to detect and denote the use of water on a bathroom session ticket. Illustrated is an embodiment of a sink 34 having sensor 36 and transmitter 38 that generates a signal received by the ticket dispenser when water is used.

Figure 8:
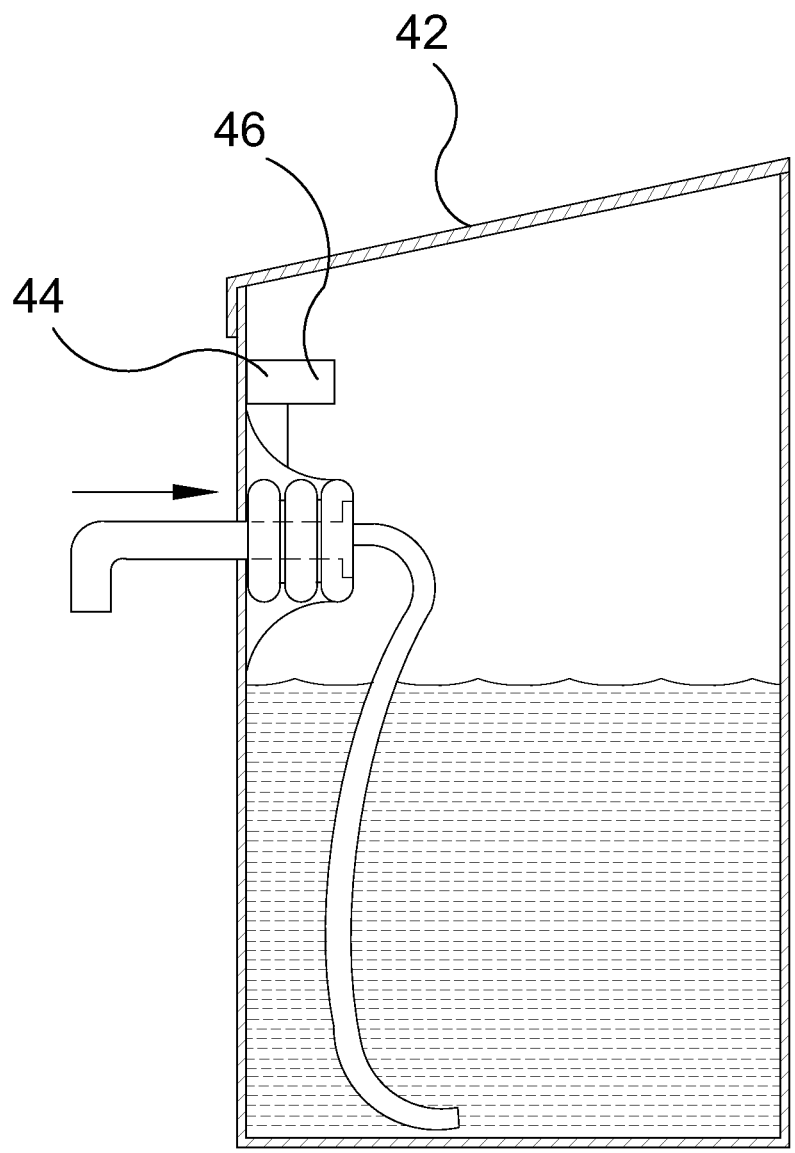
FIG. 8 is a cutaway view of a soap dispenser having a sensor to detect and denote the use of soap on a bathroom session ticket.

Referring to FIG. 8, shown is a cutaway view of a soap dispenser having a sensor to detect and denote the use of soap on a bathroom session ticket. Illustrated is an embodiment of a soap dispenser 42 having sensor 44 and transmitter 46 that generates a signal received by the ticket dispenser when soap is dispensed.

Figure 9:
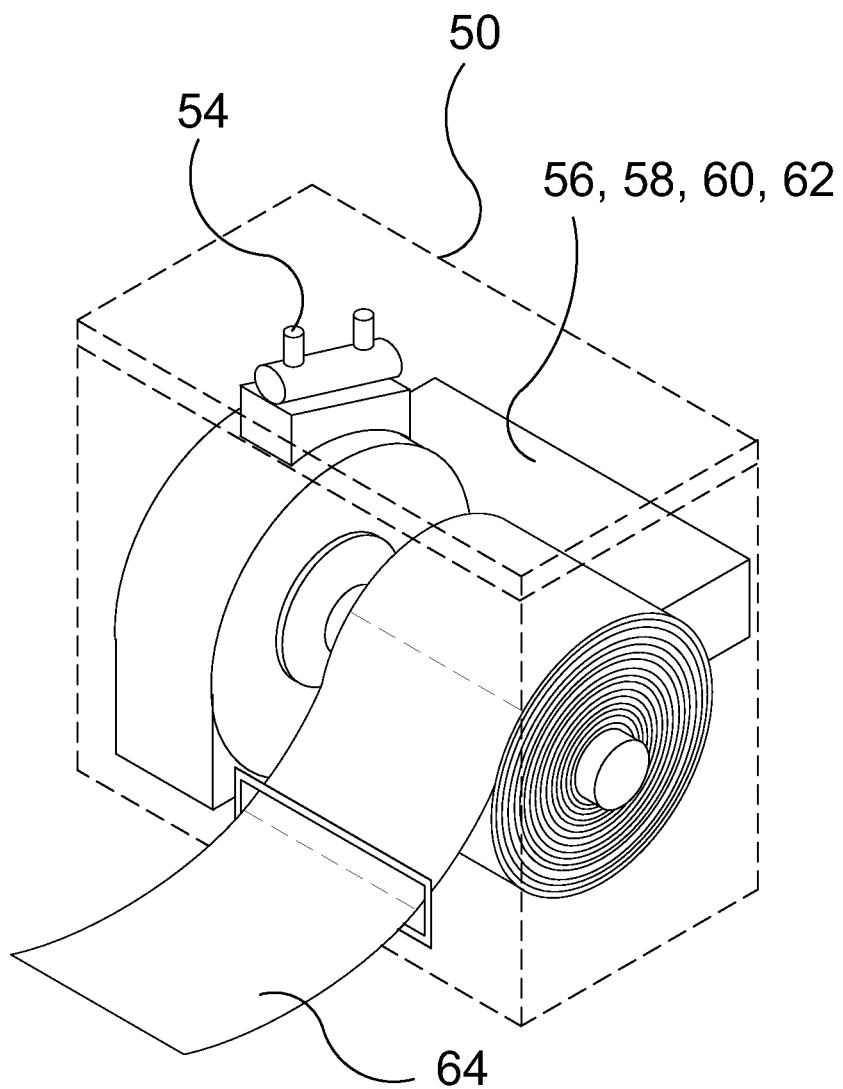
FIG. 9 is a perspective view of the ticket dispenser dispensing a bathroom session ticket.

Referring to FIG. 9, shown is a perspective view of the ticket dispenser dispensing a bathroom session ticket. Illustrated is ticket dispenser 50 having receiver 54 receiving sensor signals from the key pad, sink water and soap dispenser, which are processed by microprocessor 56 having memory 58 and software/hardware 60 that generates ticket 64 using printer 62.

Figure 10:
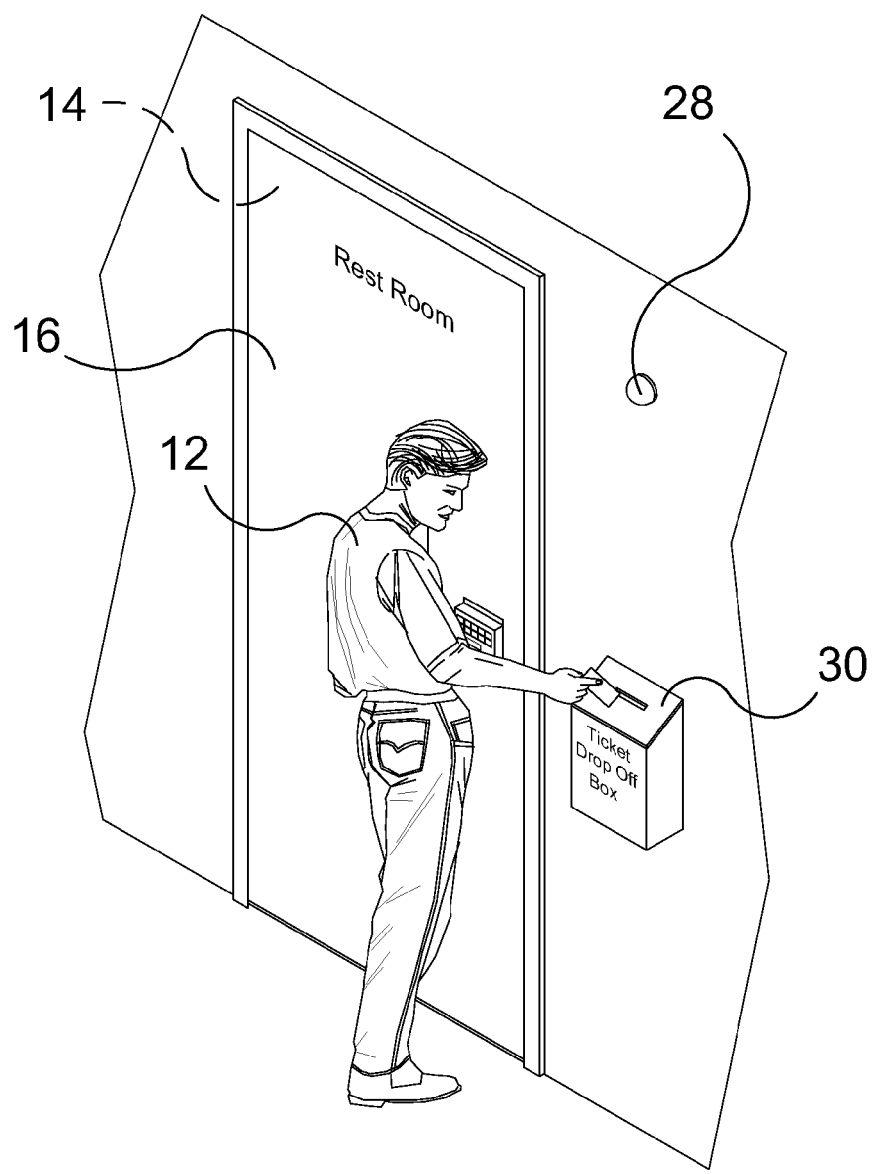
FIG. 10 is a perspective view of the user depositing a bathroom session ticket in a collection box.

Referring to FIG. 10, shown is a perspective view of the user depositing a bathroom session ticket in a collection box. The hygiene assurance system provides bathroom facility 14 having entry door 16 incorporating a lock having a key pad, occupancy indicator 28 and ticket collection box 30. When user 12 leaves bathroom facility 14 a bathroom session ticket 64 is dispensed, which is then deposited by user 12 into ticket collection box 30.

Figure 11:
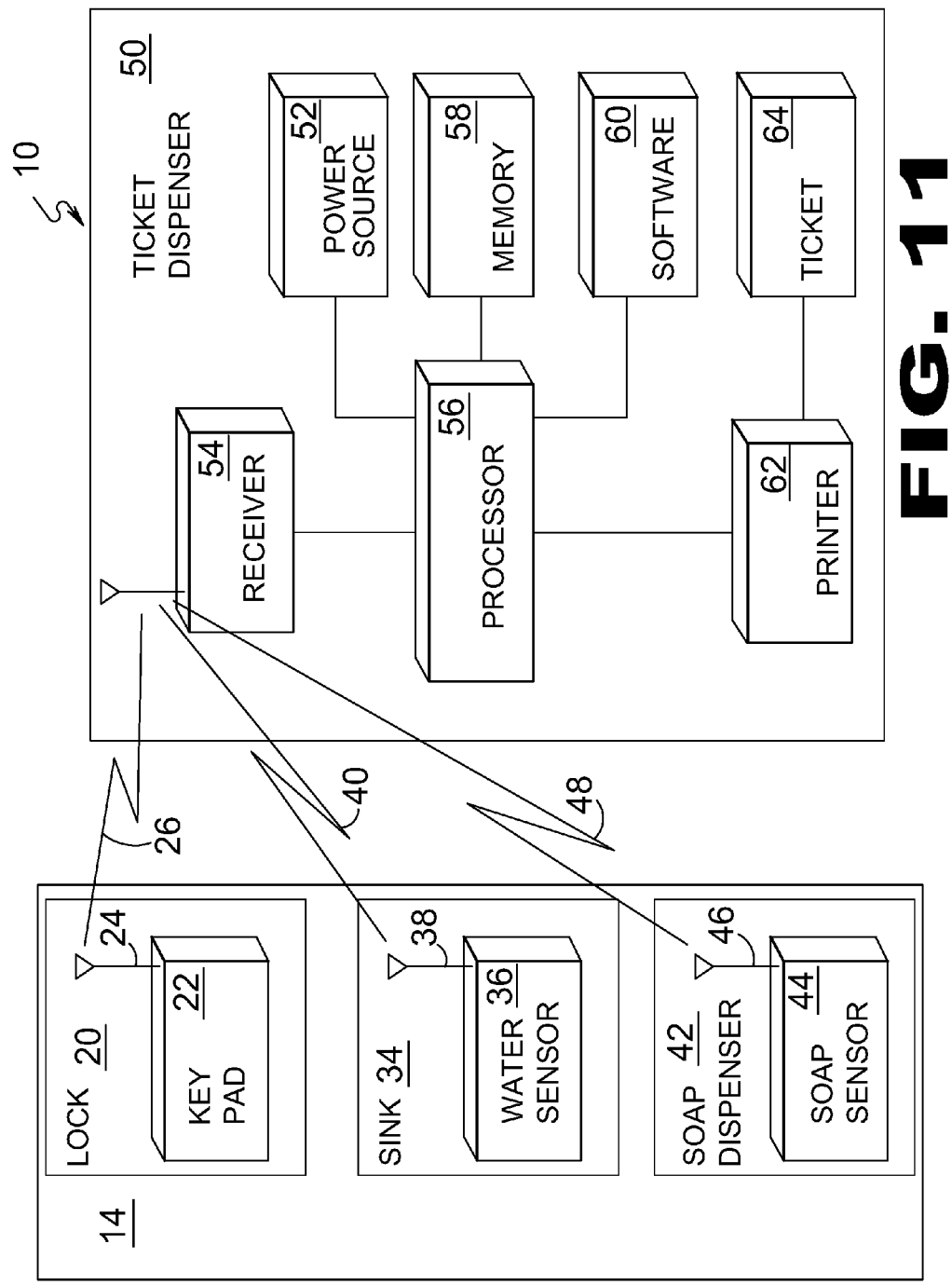
FIG. 11 is a block diagram of the components of the hygiene assurance system of the present invention.

Referring to FIG. 11, shown is a block diagram of the components of the hygiene assurance system of the present invention. The hygiene assurance system 10 of the present invention provides a bathroom facility 14 having a lock 20 with key pad 22 and transmitter 24 generating signal 26 that is received by ticket dispenser 50 receiver 54 that initiates a bathroom session ticket 64 when the user enters their key code into key pad 22, which unlatches the entry door. The facility also provides sensors for bathroom services to indicate whether soap and water where used by having a sink 34 with sensor 36 and transmitter 38 generating signal 40 received by ticket dispenser 50 receiver 54. Sensor 36 is attached to the sink water line or sink drain indicating use of sink water. Further provided is soap dispenser 42 having soap sensor 44 and transmitter 46 generating signal 48 received by ticket dispenser 50 receiver 54 indicating that soap was used during the bathroom session. Ticket dispenser 50 having power source 52 processes signals 26, 40, 48 received by receiver 54 through processor 56 having memory 58 and software/firmware 60 to generate bathroom session ticket 64 using printer 62. The ticket will then be deposited by the user into a collection box, which may be incentive enough to have employees wash their hands since the tickets may be reviewed by management for hygiene compliance.

Figure 12A:
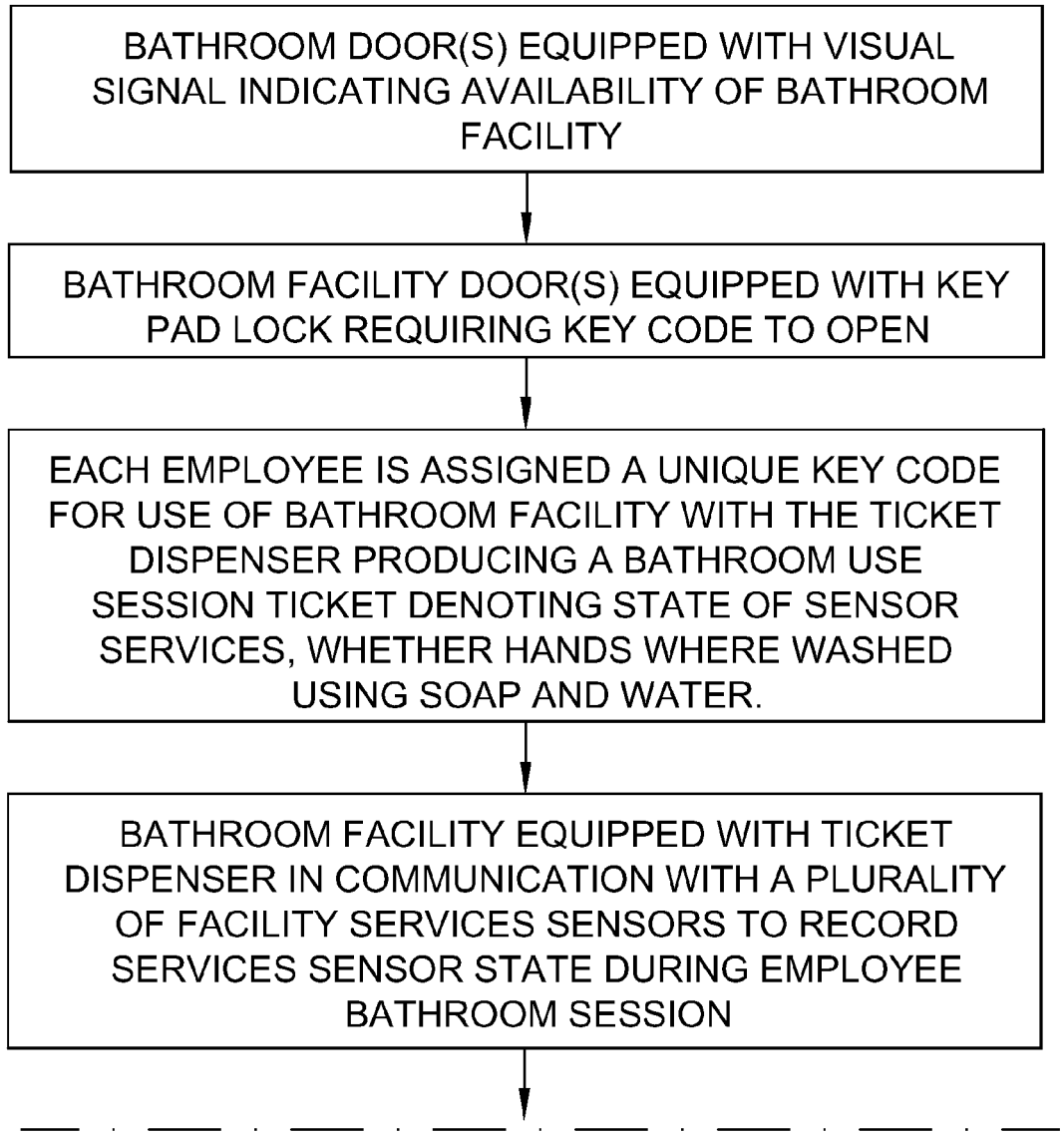
FIG. 12A is a chart of the method to ensure employee hygiene when using bathroom facility.
Figure 12B:
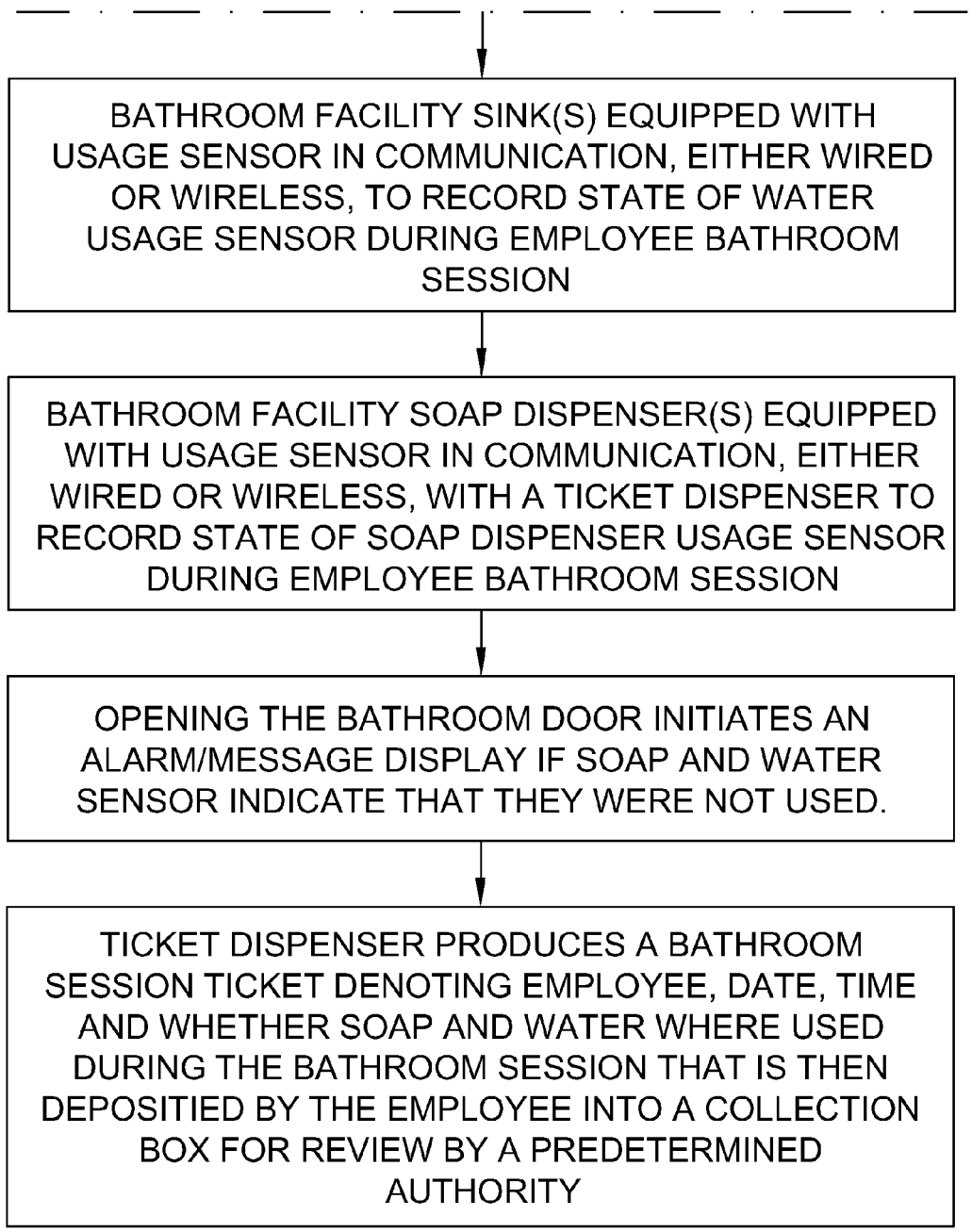
FIG. 12B is a continuation of the chart of FIG. 12A of the method to ensure employee hygiene when using bathroom facility.

Referring to FIG. 12A through 12B, shown is a chart of the method to ensure employee hygiene when using bathroom facility. To insure that employees follow a hygiene plan, the present invention provides modification to the bathroom facility having a lock with a key pad that opens when an employee enters their unique key code and initiates a bathroom session ticket. Sensors attached to the sink and soap dispenser record on the bathroom session ticket whether sink water was used and whether soap was used during the bathroom session.

Figure 13A:
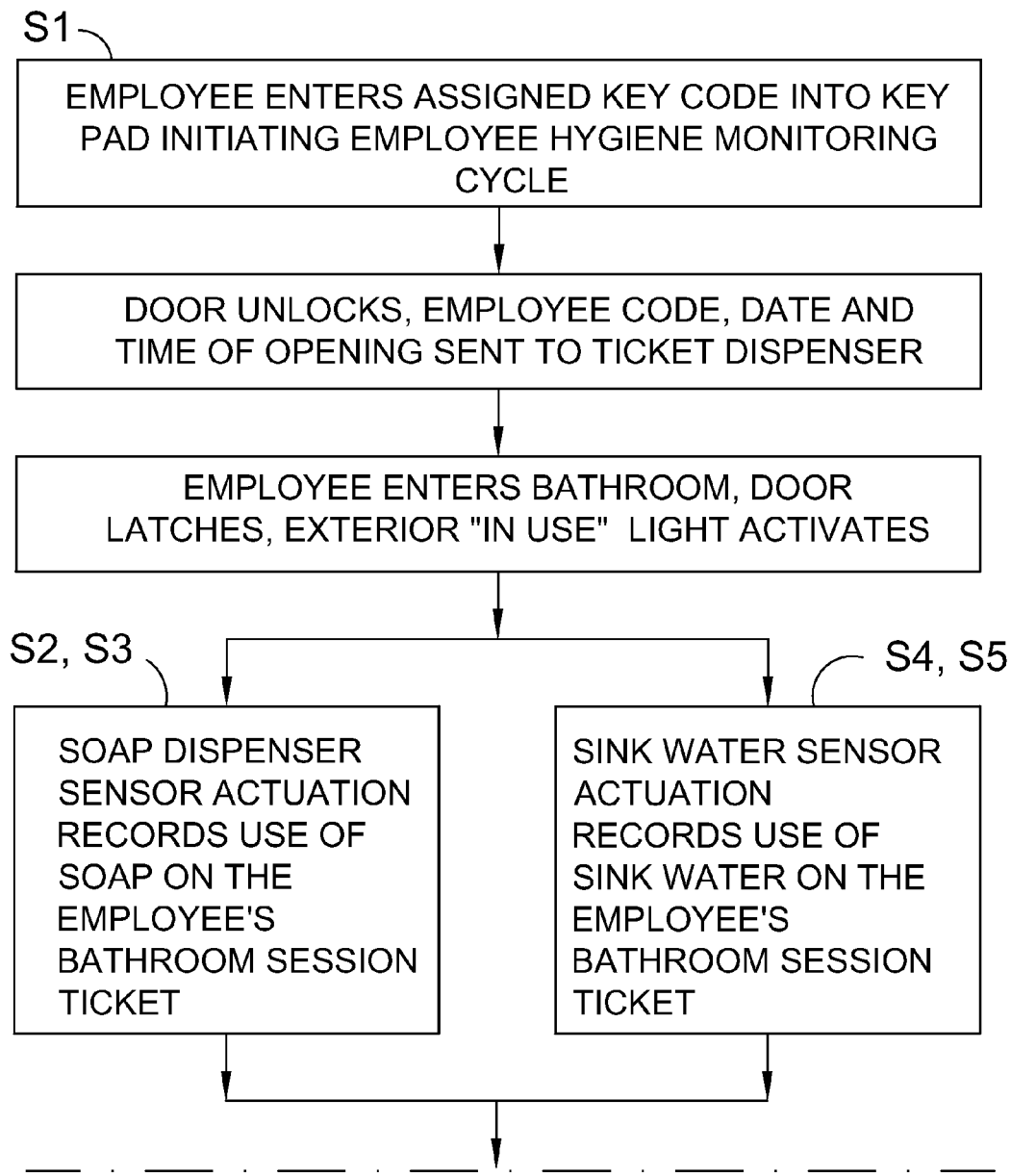
FIG. 13A is a stepwise chart depicting user and sensor interaction in generating a bathroom session ticket.
Figure 13B:
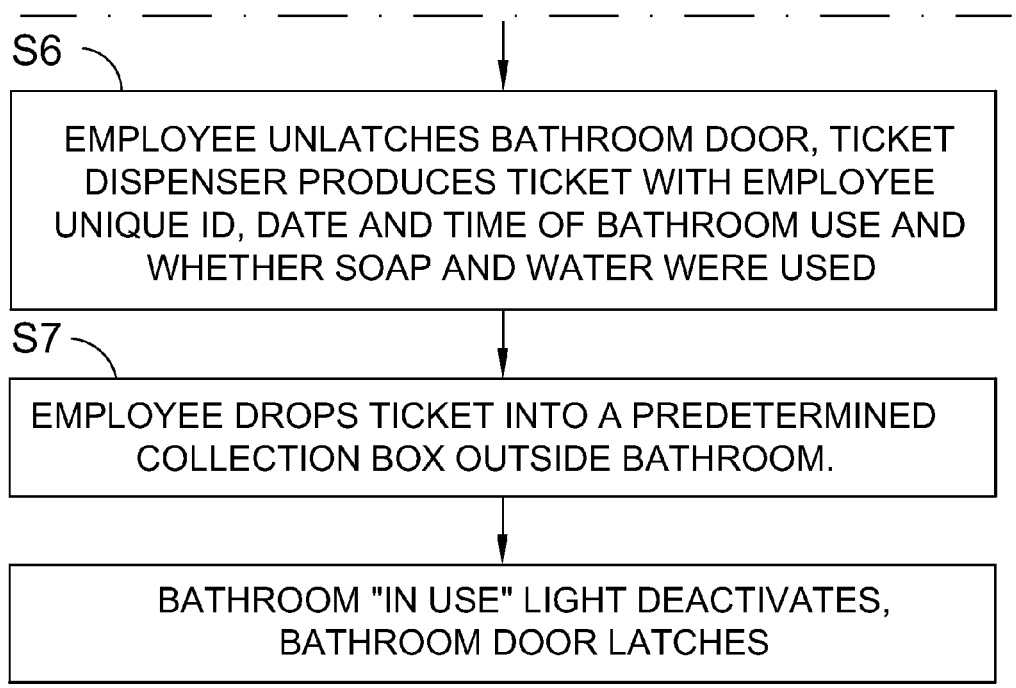
FIG. 13B is a continuation of the chart of FIG. 13A, a stepwise chart depicting user and sensor interaction in generating a bathroom session ticket.

Referring to FIG. 13A through 13B, shown is a stepwise chart depicting user and sensor interaction in generating a bathroom session ticket. The restroom facility incorporates a locked entry that requires an employee to key in their assigned key code to gain entrance into the restroom facility. A ticket dispenser within the facility is in communication with a door sensor so that when the door is unlatched a bathroom session ticket is initiated. Sink sensor and soap sensor serve as indicators that the employee washed their hands during the bathroom session. When the door is again unlatched the ticket dispenser will produce a bathroom session ticket for the employee that the employee will deposit in a collection box upon leaving the restroom.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An apparatus for monitoring hygiene of a person in a restroom, comprising:
   a lock for a door for preventing entry into a restroom without identification of a person seeking entry into the restroom;
   means for identifying the person seeking entry into the restroom including a keypad for entry of a code for identifying the person;
   means for unlocking said lock of the door for permitting entry of the person into the restroom upon identification of the person seeking entry;
   means for recording entry of the person into the restroom including a first sensor for sensing use of sink water by the person and a second sensor for sensing use of soap by the person;
   means for producing a written record evidencing the use of sink water by the person as sensed by said first sensor and the use of soap by the person as sensed by said second sensor; and,
   means for dispensing the written record to the person evidencing the use of sink water and the use of soap by the person upon exiting the restroom via the door of the restroom.

2. The apparatus for monitoring hygiene of a person in a restroom according to claim 1, wherein said means for dispensing the written record evidencing the use of sink water and the use of soap by the person includes said keypad for use by the person for identifying the person and for permitting the person to exit the restroom via the door and for initiating the dispensing of the written record to the person.

3. The apparatus for monitoring hygiene of a person in a restroom according to claim 1, further comprising an alarm actuated by said first sensor in an absence of said first sensor sensing use of sink water by the person.

4. The apparatus for monitoring hygiene of a person in a restroom according to claim 1, further comprising an alarm actuated by said second sensor in an absence of said second sensor sensing use of soap by the person.

* * * * *